United States Patent [19]
Sukigara et al.

[11] Patent Number: 5,252,999
[45] Date of Patent: Oct. 12, 1993

[54] LASER APPARATUS INCLUDING BINOCULAR INDIRECT OPHTHALMOSCOPE

[75] Inventors: Yasutaka Sukigara, Aichi; Nobuyuki Yano, Okazaki; Yasuo Ota, Gamagori, all of Japan

[73] Assignee: Nidek Co., Ltd., Aichi, Japan

[21] Appl. No.: 780,507

[22] Filed: Oct. 22, 1991

[30] Foreign Application Priority Data

Oct. 26, 1990 [JP] Japan ............................ 2-290223

[51] Int. Cl.$^5$ .............................................. A61B 3/10
[52] U.S. Cl. ..................................... 351/221; 351/205; 351/214
[58] Field of Search ................ 351/205, 214, 221; 128/645, 395, 397, 398; 606/4, 5

[56] References Cited

U.S. PATENT DOCUMENTS

| | | | |
|---|---|---|---|
| 4,477,159 | 10/1984 | Mizuno et al. | |
| 4,561,436 | 12/1985 | Munnerlyn | 128/303.1 |
| 4,580,559 | 4/1986 | L'Esperance | |
| 4,671,631 | 6/1987 | Sigelman | 351/205 |
| 4,993,827 | 2/1991 | Benedek et al. | |
| 5,067,951 | 11/1991 | Greve | 351/221 |

FOREIGN PATENT DOCUMENTS

| | | |
|---|---|---|
| 57-78852 | 5/1982 | Japan . |
| 1-236050 | 9/1989 | Japan . |
| 1-236070 | 9/1989 | Japan . |
| 1-236071 | 9/1989 | Japan . |
| 1378986 | 1/1975 | United Kingdom . |
| 2074343 | 10/1981 | United Kingdom . |
| WO84/01110 | 3/1984 | World Int. Prop. O. . |

Primary Examiner—Rodney B. Bovernick
Assistant Examiner—Hung Xuan Dang
Attorney, Agent, or Firm—Nikaido, Marmelstein, Murray & Oram

[57] ABSTRACT

This application discloses a laser apparatus including a binocular indirect ophthalmoscope for irradiating a treatment laser beam on an eye to be treated comprising, an optical fiber for guiding the treatment laser beam to the binocular indirect ophthalmoscope, an optical element, which reflects the treatment laser beam while penetrates a pair of observation beams of the binocular indirect ophthalmoscope is provided in the object side of an ophthalmoscope lens, an optical system which directs the treatment laser beam to said optical element so that the axis of the treatment laser beam coincides with the substantial center of said pair of observation beam axes, whereby the power of the treatment laser beam becomes stable owing to above constitution.

15 Claims, 3 Drawing Sheets

LASER APPARATUS INCLUDING BINOCULAR INDIRECT OPHTHALMOSCOPE

BACKGROUND OF THE INVENTION

The present invention generally relates to a laser apparatus which uses a binocular indirect ophthalmoscope fixedly mounted on the head of an operator and, more particularly, to an apparatus which is suitable for photocoagulation treatment of the peripheral portion of a patients fundus oculi.

In fundus disease treatments, there has been conventionally used a photocoagulation apparatus which is using an argon laser for photocoagulation treatment. Such a photocoagulation apparatus generally has had defects that the main device of the apparatus is large in size, a positional relationship between the apparatus and a patient's eye is substantially fixed to provide a poor handleability, a manipulator type apparatus requires an operator to use an experienced assistant in operating the apparatus, and so on.

For the purpose of solving these problems, JP-A-57-78852 discloses an apparatus wherein a beam emitted from a photocoagulation light source is guided to a binocular indirect ophthalmoscope via an optical fiber to attain a coaxial relationship with respect to an illumination optical system.

Further, in order to overcome problems caused by the large size of such laser apparatuses, there have recently been suggested laser apparatuses which use a beam emitted from a small sized semiconductor laser diode for treatment, as in JP-A 1-236070, 1-236071 and 1-236050.

With the laser apparatus of the JP-A 57-78852, a photocoagulation optical system and an illumination optical system are set to have a mutual coaxial relationship but to be shifted in its optical axis from the optical axis of an observation system. For this reason, even when an operator is observing a patient's fundus, it is difficult for the operator to judge whether or not a treatment beam is shut off by patient's pupil. Therefore, such a laser apparatus has been defective in that, in a treatment requiring a predetermined level of beam power, when the operator cannot perform the treatment because of its insufficient power, it is hard for the operator to judge whether the impossible treatment results from the treatment beam shut off by the patient's pupil or from the deterioration of the apparatus itself. Further, when such a laser emitting a beam of a large divergence angle as a semiconductor laser is employed, a beam passing through the pupil becomes diverged correspondingly widely and thus the amount of beam shut off by the iris becomes also large. Furthermore, since the semiconductor laser emits a beam with a wavelength of about 800 nm, the absorption of the beam at the fundus is low. In addition, output power transmitted by a binocular indirect ophthalmoscope is relatively small, and the shut-off of the beam at the iris disadvantageously tends to cause an insufficient power. Conversely, when the output is adjusted while the laser beam is shut off by the iris or the like so that the laser beam is irradiated at such a position as immune to such shut-off, the power may become too strong.

SUMMARY OF THE INVENTION

It is an object of the present invention to provide a laser apparatus which allows operator to treat a diseased part of a patient observed in his observation field with stable laser power.

Another object of the present invention is to provide a laser apparatus, even when emitting a treatment beam of relatively low power level, which allows an operator to conduct necessary treatment with a simple handling procedure through the efficient use of the beam.

In accordance with the present invention, the above objects can be attained by providing a laser apparatus which has such arrangements and features which follow.

In an aspect of the present invention, there is provided a laser apparatus for irradiating a treatment laser beam on an eye to be treated through an ocular lens, which apparatus comprises a binocular indirect ophthalmoscope to be fixedly mounted on operator's head or the like part, an optical fiber for guiding a light beam emitted from a treatment laser light source to the binocular indirect ophthalmoscope, and an optical member for making an optical axis of a light beam emitted from the optical fiber coincide substantially with an optical axis of an observation system of the binocular indirect ophthalmoscope.

In the present invention, the treatment laser light source is a semiconductor laser.

In the invention, the optical member for making the optical axis of a light beam emitted from the optical fiber coincide substantially with the optical axis of an observation system is a dichroic mirror.

In the present invention, the treatment light beam emitted from the treatment laser light source is adjusted with respect to an illumination beam and then the treatment light beam and the illumination beam are sent into the beam guiding optical fiber.

In the invention, the treatment apparatus for irradiating a treatment laser beam on an eye to be treated through an ocular lens, further comprises means for continuously adjusting an operational distance.

In the invention, the above means for continuously adjusting the operational distance includes an auxiliary lens in an optical path and means for moving the auxiliary lens in its optical axis direction.

DESCRIPTION OF THE PREFERRED EMBODIMENTS

An embodiment of the present invention will be described in detail with reference to the accompanying drawings.

Figure 1:
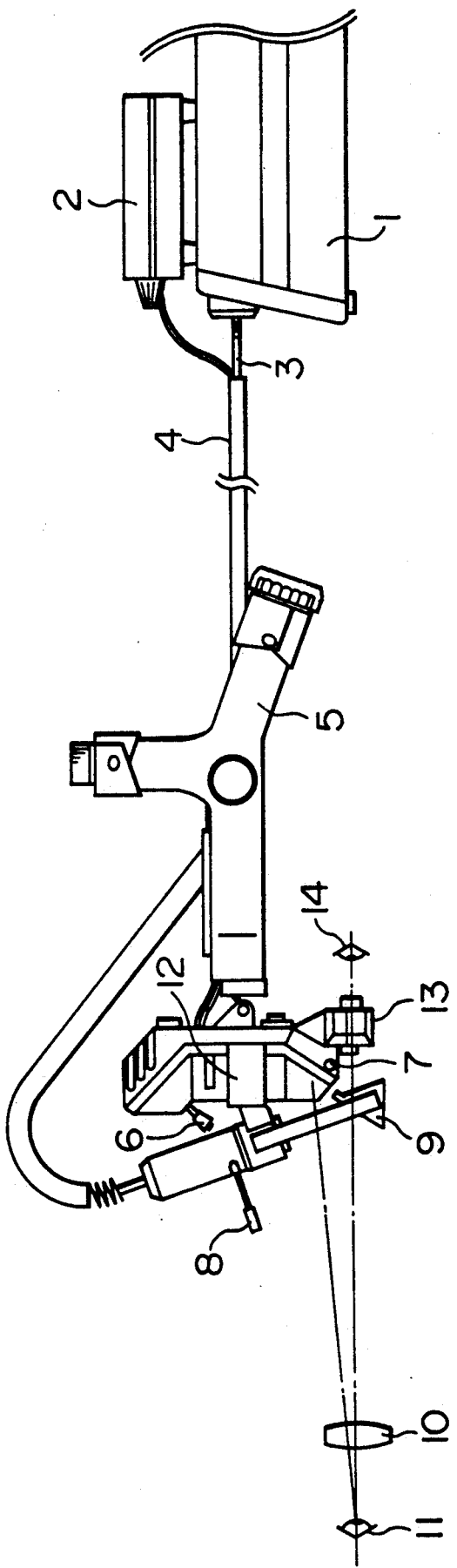
FIG. 1 is a schematic exterior appearance view of an apparatus in accordance with an embodiment of the present invention, as viewed from its side.
Figure 2:
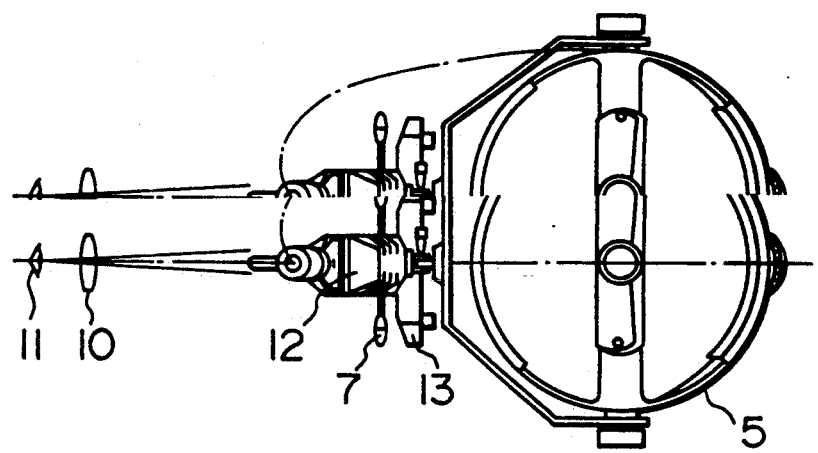
FIG. 2 is a view of the apparatus as viewed from its top.

Referring first to FIGS. 1 and 2, FIG. 1 is a schematic exterior appearance view of an apparatus of the present invention as viewed from its side, and FIG. 2 is a view of the apparatus when viewed from its top. Reference numeral 1 denotes a main device of a treatment apparatus which incorporates light sources including a semiconductor laser diode used to emit a treatment beam and a He-Ne laser used to emit a guide beam, and also incorporates an optical system (to be detailed later) for coupling these laser beams and transmitting them to an optical fiber.

Numeral 2 is an illumination power supply and 3 denotes an optical fiber for guiding a laser beam. The optical fiber 3 and a power supply card of the illumination power supply 2 are inserted into a bifurcated cable 4 for their protection. Numeral 5 represents a fastening band for fastening a binocular indirect ophthalmoscope on operator's head, 6 a change-over knob for switching the intensity of an illumination light, 7 an up/down position adjusting knob for adjusting the up and down positions of the illumination light, 8 a working distance adjusting knob. Further, numeral 9 denotes a dichroic mirror having characteristics of reflecting infrared rays and penetrating visual rays. Since the diode laser has a wavelength of 800 nm and the He-Ne laser has a wavelength of 632.8 nm, such a dichroic mirror is selected that has characteristics of reflecting substantially 100% of incident rays in the vicinity of 800 nm and partly reflecting and partly penetrating the incident rays at 632.8 nm. In the present embodiment, there is employed such a dichroic mirror that can reflect 98% of incident rays at around 800 nm and 50% thereof at 632.8 nm and also can penetrate more than 50% visual rays in a wavelength range of 400-700 nm. Reference numeral 10 denotes an ophthalmoscope lens which usually comprises an aspherical lens for magnifying patient's eye 11. Numeral 12 denotes an illumination unit which houses an optical system for illuminating the interior of the patient's eye 11, 13 denotes an observation unit which houses an observation optical system, 14 denotes operator's eye.

Figure 3:
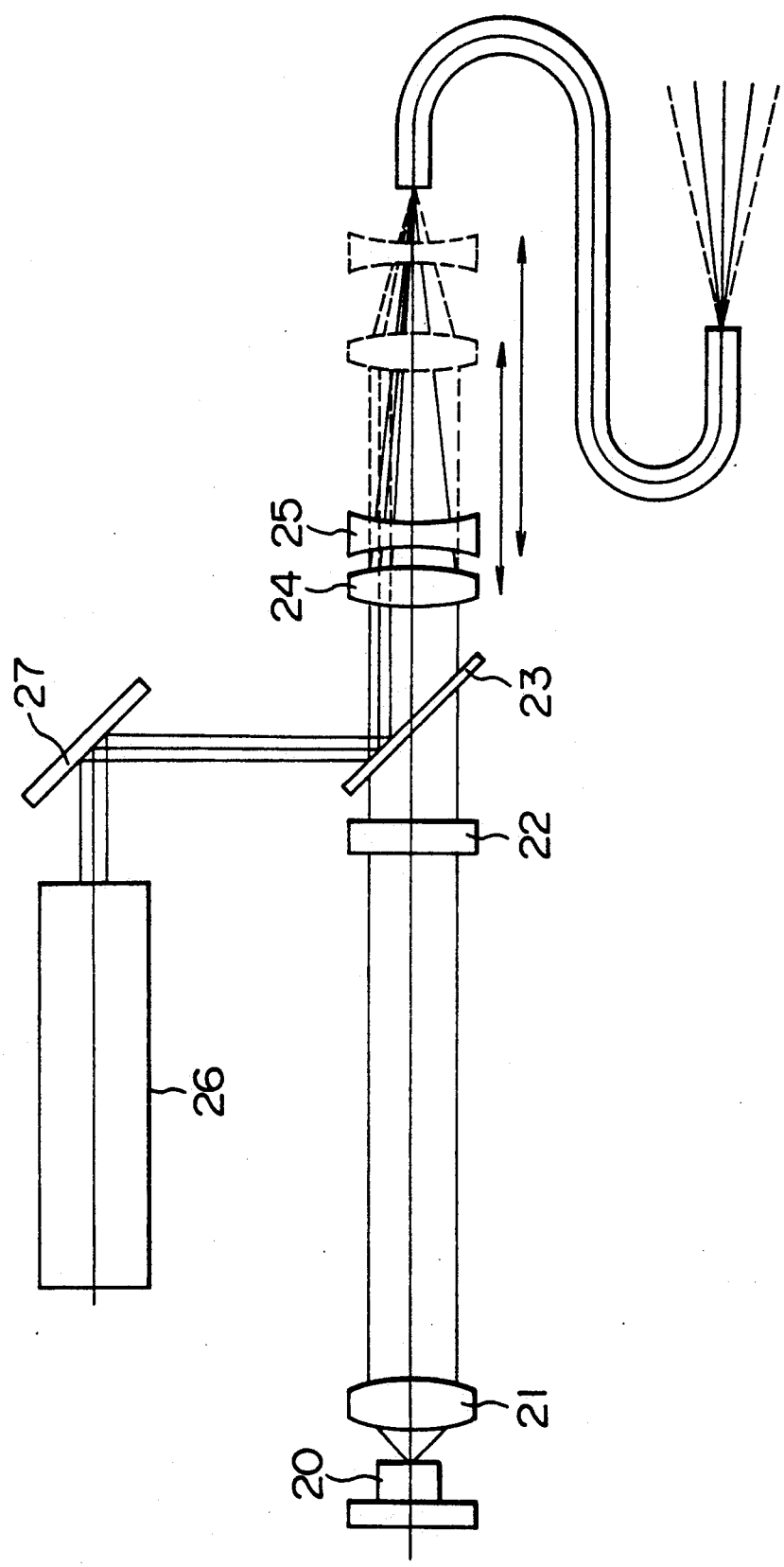
FIG. 3 is an arrangement of an optical system of a main device of the treatment apparatus.

Shown in FIG. 3 is an arrangement of the optical system in the main device of the treatment apparatus, in which a laser beam emitted from a light source 20 as a laser diode is passed through a collimating lens 21 to form a parallel or collimated beam in a certain direction. A laser beam emitted from a semiconductor laser has an astigmatism and thus when the beam directed to the output side of the collimating lens 21 is passed through a cylindrical lens 22, an output beam from the lens 22 becomes also a collimated beam in the other direction.

Reference numeral 23 denotes a dichroic mirror which has characteristics of penetrating the diode laser beam and reflecting a beam from a He-Ne laser, 24 and 25 denote movable lenses. The resultant focal distance of the combined movable lenses 24 and 25 can be varied by changing a distance between these lenses 24 and 25. In this connection, however, the distance change is controlled so that the resultant image focal distance will not be changed.

Further, reference numeral 26 is a He-Ne laser light source and 27 is a mirror. A laser beam as a sight beam emitted from the He-Ne laser 27 is combined with the diode laser beam from the laser diode 20 by the dichroic mirror 23. However, the He-Ne laser beam is decentered for the purpose of making the divergence angle of the beam emitted from the optical fiber coincide with that of the diode laser beam.

Figure 4:
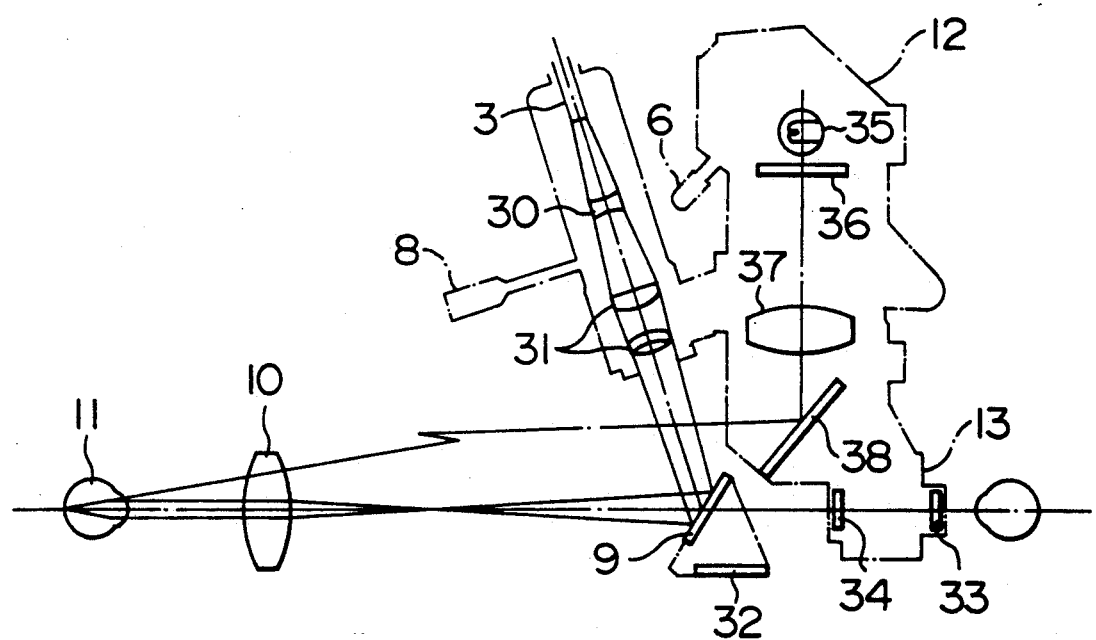
FIG. 4 is an arrangement of an optical system of a binocular indirect ophthalmoscope in the apparatus.
Figure 5:
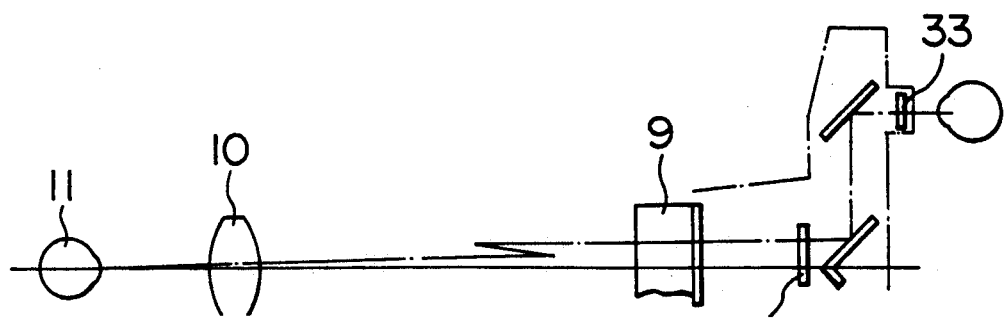
FIG. 5 is a view of a part of the optical system of FIG. 4 as viewed from its top.

FIG. 4 is an arrangement of the optical system of the binocular indirect ophthalmoscope in the treatment apparatus, and FIG. 5 is a view of a part of the optical system as viewed from its top side.

A combined beam of the diode laser beam and the He-Ne laser beam emitted from the main device 1 of the treatment apparatus is directed through the optical fiber 3 to an auxiliary lens 30 to be diverged thereat, converged through a lens group 31 of two convex lenses, and then reflected by the dichroic mirror 9, so that the optical axis of the above optical system coincides with that of the observation treatment laser optical system. A light shielding plate 32 is provided to protect operator's body from being exposed to the He-Ne laser beam partly passed through the dichroic mirror 9.

The laser beam set to have the same optical axis as the observation optical system is once focused in front of the ophthalmoscope lens 10 and then directed toward the patient's eye 11.

When it is desired to perform a photocoagulating treatment through the binocular indirect ophthalmoscope, a vitreous body is often subjected to an air substitution after surgery of the vitreous body, in which case the refractive power of the patient's eye varies largely depending on the presence or absence of water in the anterior chamber. Accordingly, in the present embodiment, in order to avoid this, the working distance adjusting knob 8 is moved up or down according to the refractive power of the patient's eye so that the auxiliary lens 30 is moved in its optical axis direction to thereby change the focal distance of the lens 30 and continuously vary the working distance.

In FIGS. 4 and 5, reference numeral 33 denotes an ocular lens for observation of the patient's eye and numeral 34 denotes an operator protection filter for protecting the operator's eye 14 from the laser beam reflected by the patient's eye 11, which form the aforementioned observation optical system. An illumination lamp 35 emits light which is passed through an illumination diaphragm 36 and a condenser lens 37, reflected by a mirror 38 and then illuminated onto the patient's eye 11. The intensity of illumination light is adjusted by means of the illumination diaphragm change-over knob 6, while the up and down positions of the illumination light is adjusted by means of the up/down position adjusting knob 7.

Explanation will next be briefly made as to the operation of the embodiment having such an arrangement as mentioned above. An operator fixedly mounts the binocular indirect ophthalmoscope on his head by means of the fastening band 5 and then finely adjusts the illumination light with use of the illumination diaphragm change-over knob 6 and the up/down position adjusting knob 7. The operator observes the patient's eye 11 while holding the ophthalmoscope lens 10 in front of the patient's eye 11. After confirming patient's diseased part, the operator makes the guide beam coincide with the diseased part, and moves the working distance adjusting knob 8 in its up or down direction to thereby move the auxiliary lens 30 in its optical axis direction and adjust the working distance. After completing the adjustment of the working distance, the operator turns ON a trigger switch through a foot switch (not shown) to irradiate the treatment beam onto the diseased part for its treatment. It is desirable that the foot switch can be movable together with operator's movement.

The semiconductor laser beam is selected as a treatment beam in above embodiment, an apparatus using other type of laser beam, e.g. argon laser beam, can perform as well as above embodiment.

In accordance with the present invention, a minimum number of lenses can be required in the optical system, and the diseased part observed by the operator can be stably treated by a treatment beam at a sufficient power level without being shut off by the patient's pupil.

Further, since the working distance can be adjusted by an suitable external lever, the operator can conduct a treating operation on the diseased part with use of the binocular indirect ophthalmoscope which is originally used to observe an eye having a normal structure, as in the case of the normal eye. For example, the operator can easily match the treatment beam with the fundus regardless of the condition of a vitreous body subjected to the air substitution after its surgery or the presence or absence of water in the anterior chamber.

What is claimed is:

1. A laser apparatus including a binocul indirect opthalmoscope for irradiating a treatment laser beam on an eye to be treated comprising:
    an optical fiber for guiding the treatment laser beam to the binocular indirect opthalmoscope;
    an optical element, which reflects the treatment laser beam while transmitting a pair of observation beams of the binocular indirect opthalmoscope, provided in the object side of an opthalmoscope lens;
    an illumination optical system providing an illumination beam at a predetermined angle to a plane defined by optical axes of said pair of observation beams; and
    an optical system which directs the treatment laser beam to said optical element so that the optical axis of the treatment laser beam coincides with the substantial center of said optical axes of said pair of observation beams.

2. A laser apparatus according to claim 1, wherein the treatment laser beam is a laser beam for photocoagulation.

3. A laser apparatus according to claim 2, the laser beam for photocoagulation is semiconductor laser beam.

4. A laser apparatus according to claim 1, wherein the optical element is a dichroic mirror.

5. A laser apparatus according to claim 1, further comprising means for irradiating the eye to be treated by a guide beam, the treatment laser beam and the guide beam are coupled and sent into the optical fiber.

6. A laser apparatus according to claim 1, wherein said illumination optical system provides said illumination beam at a predetermined angle such that said illumination beam enters the eye to be treated at an angle to the optical axes of said pair of observation beams and said treatment laser beam.

7. A laser apparatus including a binocular indirect opthalmoscope for irradiating a treatment laser beam on an eye to be treated comprising:
    an optical fiber for guiding the treatment laser beam to the binocular indirect ophthalmoscope;
    an optical element, which reflects the treatment laser beam while transmitting a pair of observation beams of the binocular indirect opthalmoscope is provided in the object side of an ophthalmoscope lens;
    an illumination optical system providing an illumination beam at a predetermined angle to a plane defined by optical axes of said pair of observation beams;
    an optical system which directs the treatment laser beam to said optical element so that the optical axis of the treatment laser beam coincides with the substantial center of said optical axes of said pair of observation beams; and
    means for continuously adjusting an optical distance of the treatment laser beam.

8. A laser apparatus according to claim 7, wherein the continuous adjusting means includes an auxiliary lens in an optical path of the treatment laser beam and means for moving the auxiliary lens in its optical axis direction.

9. A laser apparatus according to claim 7, wherein the continuous adjusting means includes a working distance adjusting knob disposed on a body of the laser apparatus and operable by an operator.

10. A laser apparatus including a binocular indirect ophthalmoscope for irradiating a treatment semiconductor laser beam on an eye to be treated comprising:
    an optical fiber for guiding the semiconductor laser beam to the binocular indirect ophthalmoscope;
    an optical element, which reflects the semiconductor laser beam while transmitting a pair of observation beams of the binocular indirect ophthalmoscope, provided in the object side of an ophthalmoscope lens;
    an optical system which directs the semiconductor laser beam to the optical element so that the optical axis of the semiconductor laser beam coincides with the substantial center of optical axes of said pair of observation beams; and
    an illumination optical system providing an illumination beam at a predetermined angle to a plane defined by the optical axes of said pair of observation beams.

11. A laser apparatus according to claim 10, further comprising means for irradiating the eye to be treated by a guide beam, the treatment beam and the guide beam being coupled and sent into the optical fiber.

12. A laser apparatus according to claim 10, further comprising means for continuously adjusting an optical distance of the treatment laser beam.

13. A laser apparatus according to claim 10, wherein said illumination optical system provides said illumination beam at a predetermined angle such that said illumination beam enters the eye to be treated at an angle to the optical axes of said pair of observation beams and said semiconductor laser beam.

14. A laser apparatus including a binocular indirect ophthalmoscope for irradiating a treatment laser beam on an eye to be treated comprising:
    an optical fiber for guiding the treatment laser beam to the binocular indirect ophthalmoscope;
    an optical element, which reflects the treatment laser beam while transmitting a pair of observation beams of the binocular indirect ophthalmoscope is provided in the object side of an ophthalmoscope lens;
    an illumination optical system providing an illumination beam at a predetermined angle to a plane defined by optical axes of said pair of observation beams;
    an optical system which directs the treatment laser beam to said optical element so that the optical axis of the treatment laser beam coincides with the substantial center of said optical axes of said pair of observation beams; and
    means for irradiating the eye to be treated by a guide beam, the treatment laser beam and the guide beam are coupled and sent into the optical fiber.

15. A laser apparatus including a binocular indirect ophthalmoscope for irradiating a semiconductor laser beam on an eye to be treated comprising:

an optical fiber for guiding the semiconductor laser beam to the binocular indirect ophthalmoscope;

an optical element, which reflects the semiconductor laser beam while transmitting a pair of observation beams of the binocular indirect ophthalmoscope, provided in the object side of an ophthalmoscope lens;

an optical system which directs the semiconductor laser beam to the optical element so that the optical axis of the semiconductor laser beam coincides with the substantial center of optical axes of said pair of observation beams;

an illumination optical system providing an illumination beam at a predetermined angle to a plane defined by the optical axes of said pair of observation beams; and means for irradiating the eye to be treated by a guide beam, the treatment beam and the guide beam being coupled and sent into the optical fiber.

* * * * *